United States Patent [19]

Huth et al.

[11] E Patent Number: Re. 32,672

[45] Reissued Date of Patent: May 24, 1988

[54] METHOD FOR SIMULTANEOUSLY CLEANING AND DISINFECTING CONTACT LENSES USING A MIXTURE OF PEROXIDE AND PROTEOLYTIC ENZYME

[75] Inventors: Stanley W. Huth, Mission Viejo; Sam W. Lam; Richard M. Kiral, both of Irvine, all of Calif.

[73] Assignee: Allergan, Inc., Irvine, Calif.

[21] Appl. No.: 82,860

[22] Filed: Aug. 4, 1987

Related U.S. Patent Documents

Reissue of:

[64] Patent No.: 4,670,178
Issued: Jun. 2, 1987
Appl. No.: 774,193
Filed: Sep. 9, 1985

[51] Int. Cl.[4] ..... C11D 7/42; C11D 7/54

[52] U.S. Cl. ..... 252/95; 252/105; 252/106; 252/174.12; 252/DIG. 12; 252/DIG. 14; 424/130; 514/840

[58] Field of Search ..... 252/95, 106, 174.12, 252/DIG. 12, DIG. 14; 424/130; 514/840

[56] References Cited

U.S. PATENT DOCUMENTS

| | | | |
|---|---|---|---|
| 3,553,139 | 1/1971 | McCarty | 252/95 |
| 3,714,050 | 1/1973 | Gray | 252/99 |
| 3,789,001 | 1/1974 | Painelli | 252/99 |
| 3,816,319 | 6/1974 | Sarot | 252/95 |
| 3,908,680 | 9/1975 | Krezanoski | 134/27 |
| 3,910,296 | 10/1975 | Karageozian et al. | 134/2 |
| 4,096,870 | 6/1978 | Manfuso | 134/28 |
| 4,155,868 | 5/1979 | Kaplan et al. | 252/95 |
| 4,285,738 | 8/1981 | Ogata | 134/26 |
| 4,421,668 | 12/1983 | Cox et al. | 252/174.12 |
| 4,470,919 | 9/1984 | Goffinet et al. | 252/102 |
| 4,472,550 | 9/1984 | Rosenbaum et al. | 424/94 |
| 4,521,254 | 6/1985 | Anderson et al. | 134/26 |
| 4,521,375 | 6/1985 | Houlsby | 422/29 |
| 4,539,132 | 9/1985 | Oakes | 252/95 |
| 4,585,488 | 4/1986 | Giefer | 134/27 |

FOREIGN PATENT DOCUMENTS

| | | |
|---|---|---|
| 2527534 | 1/1976 | Fed. Rep. of Germany . |
| 140669 | 5/1985 | European Pat. Off. . |
| 64303 | 5/1975 | Japan . |
| 1500707 | 2/1978 | United Kingdom . |
| 2129458A | 5/1984 | United Kingdom . |
| 2139260A | 11/1984 | United Kingdom . |

OTHER PUBLICATIONS

Johansen et al., "The Degradiation of the B-Chain of Oxidized Insulin by Two Subtilisins and Their Succinylated and N-Carbamylated Derivatives," Compt. Rend., Trav. Lab. Carlsberg 1968; 36(21): 365-84.

Okunuki et al., "Specificity of Crystalline Bacterial Proteinase," J. Biochem. (1956); 43(6): 857-65.

Hagihara et al., "Crystalline Bacterial Proteinase III. Comparison of Crystalline Proteinase of Bacillus Subtilis with Crystalline Trypsin," J. Biochem. (1958) 45(5): 305-11.

White et al, "Principles of Biochemistry," Fourth Edition New York, McGraw-Hill 1968:144.

Novo Industri Information Bulletin, 169b-GB 1978; March:8.

Berg et al., "Enzymes as Detergent Components," Detergent Chemistry: Current Topics from Research and Development, (Dusseldorf, West Germany): Alfred Huthig Verlag Heidelberg, (1976) pp. 155-178.

Enkelund, "Interaction Between Proteolytic Enzymes and Detergent Components," In: Chemistry, Biochemistry and Applications Technology of Surfactants, vol. IIIC., Munich: Carl Hanser Verlag, 1973:251-65.

Oldenroth, "Comparative Examination of Different Enzymes in a Washing Agents" Fats, Soaps, Coatings, vol. 72, No. 7, 1970, pp. 582-587.

Jaag, "On a New Practical Procedure for the Determination of Activity of Enzymes Used in Washing Agents," Fats, Soaps, Coatings, vol. 71, No. 11, 1969, pp. 961-966.

Weig, "Enzymes in Washing Powders," Process Biochemistry, 1969; Feb.: 30-34.

Wedler, "Analysis of Biomaterials Deposited on Soft Contact Lenses," J. Biomed. Mater. Res. 1977; 11:525-35.

Brot et al., "Biochemistry and Physiological Role of Methionine Sulfoxide Residues in Proteins," Arch. Biochem. & Biophysics 1983; 223(1): 271-81.

Neher et al., "Interaction Between Blood and Oxygenating Bleaching Agents and Problems Involving Enzyme-Containing Washing Agents," Fats, Soaps, Coatings, vol. 72, No. 3, 1970, pp. 192-199.

Stauffer et al., "The Effect on Subtilisin Activity of Oxidizing a Methionine Residue," J. Biol. Chem. 1969; 244(19): 5333-8.

Lo, Jia-Ruey, Silverman, H. I., Korb, D. R., Am. Opt. Assoc., vol. 40, #11, 1106-1109 (1969).

*Primary Examiner*—Prince E. Willis

*Attorney, Agent, or Firm*—Finnegan, Henderson, Farabow, Garrett & Dunner

[57] ABSTRACT

A one step method for cleaning and disinfecting contact lenses is accomplished by immersing the lenses in a solution containing peroxide and a peroxide-active enzyme.

15 Claims, No Drawings

METHOD FOR SIMULTANEOUSLY CLEANING AND DISINFECTING CONTACT LENSES USING A MIXTURE OF PEROXIDE AND PROTEOLYTIC ENZYME

Matter enclosed in heavy brackets [ ] appears in the original patent but forms no part of this reissue specification; matter printed in italics indicates the additions made by reissue.

BACKGROUND

This invention relates to a method and composition for cleaning and disinfecting contact lenses. More specifically, this invention covers the simultaneous cleaning and disinfecting of contact lenses by means of a solution containing a mixture of peroxide and peroxide-active enzymes, particularly proteolytic enymes.

RELATED ART

The evolution of contact lenses from glass to the present extended wear lenses based on hydrophilic polymeric materials has provided a shifting and changing need for new and more effective means for cleaning and disinfecting such lens materials to maintain optical clarity, wearability and prevent the transfer of infectious agents into the eye.

Glass and the early polymers such as polymethylmethacrylate (PMMA) lenses could be readily cleaned by manual means using detergent because of their rigidity and hydrophobic character. While such materials are, to a certain degree, wetted by the naturally occurring aqueous layer on the eye and tears, they are lipophilic to a degree such that all soils, with the possible exception of lipids, are readily removed by manual cleaning with detergents. Hydrophilic materials, particularly polypeptides and enzymes such as lysozyme do not adhere significantly to these materials and are readily removed by cleaning with surfactants and detergents.

Glass and PMMA based contact lenses are also readily disinfected by detergent cleaning means. Mechanical cleaning processes readily remove adhered infectious materials. Secondly, since these types of materials are non-porous, chemical disinfectants can be included in storage and cleaning solutions without absorption of the disinfectant into the lens and leaching of this disinfectant into the eye during wear. Thus, there is minimal concern about the physical removal of infectious agents and the maintaining of sterility by chemical means during storage and in maintaining the sterility of cleaning, wetting and storing solutions.

Advances in polymer technology have provided significant increases in wearer comfort and eye health, but have resulted in novel problems for cleaning and disinfecting such materials.

A lens is most comfortable on the eye when the surface is wettable by eye fluid and tear solution. In all contact lens polymers now in use, except for the PMMA lenses, the lens surface is naturally hydrophilic or treated to make it hydrophilic. This is achieved by means of multiple negative charges, usually carboxylate in form, and neutral groups which provide a hydrophilic environment readily wetted by the fluid layer covering the cornea. Such negatively charged hydrophilic surfaces are present not only on the hydrogel lenses but also on more rigid lenses such as the organosiloxane-methacrylate lenses (Polycon® and silicone elastomer based lenses. In this latter category, the silicone elastomer lenses, the hydrophobic surface is coated or otherwise treated to render the surface hydrophilic.

Proteinaceous materials adsorbs to the hydrophilic lens surface during day-to-day wear. On all but purely PMMA lenses, the adsorption is so strong that even with lenses such as the rigid polysiloxane/methylmethacrylate copolymers, manual detergent cleaning methods do not adequately remove this accretion. So-called hydrogel lenses, those materials prepared from hydroxyethylmethacrylate, hydroxyethylmethylmethacrylate, vinylpyrrolidone and glycerolmethacrylate monomers and methacrylic acid or acid esters, and which absorb a significant amount of water, i.e., 35–80 percent water, are so fragile that mechanical cleaning means is not a practical way of removing soilant, particularly the strongly absorbed proteinaceous materials.

The resultant is that over time, the buildup of such materials can result in wearer discomforts and, more importantly, interfere with the optical characteristics of the lenses, particularly reduced light transmission and increased light defraction. Also, protein buildup results in eye irritation, loss of visual acuity, lens damage and in certain instances there may result a condition called giant papillary conjunctivitis.

Research has determined that the primary source of this protein build-up is the lysozyme enzyme. Additionally there may be lipoproteins and mucopolysaccharides adsorbed onto the lens surface, but proteins per se, particularly lysozyme materials are the major source of lens protein accretions. These enzymes, along with minor amounts of similar proteins, lipoproteins and mucopolysaccharides accumulate on the surface of hydrophilic lens materials.

The only safe and effective means found to date for removing this accretion is the use of enzymes, whose hydrolytic activity reduce the proteinaceous materials to small, water soluble subunits. Particularly useful are proteolytic enzymes, proteases, which hydrolyze amide bonds to break proteins down into amino acids and very small polypeptides. These protein fragments are generally water soluble and thus are easily solubilized by the surrounding aqueous environment. U.S. Pat. No. 3,910,296 discloses the use of proteases for cleaning contact lenses. See also U.S. Pat. No. 4,285,738. Enzymes with lipolytic and or mucolytic activity are also of use in discrete amounts with proteolytic enzymes for lens cleaning.

A second problem with gas permeable contact lenses, especially the hydrogel or high-water contact lenses made from HEMA, VP and GMA monomers, are concerns with disinfecting and maintaining the sterility of the lenses and lens storage solutions.

A number of methods have been devised for disinfecting lenses, including the use of high temperature, sterile saline solution washes and chemicals, e.g., antimicrobial drugs or oxidation processes.

Heat has been effective to a substantial degree but has the drawbacks of making additional cleaning more difficult, i.e., denaturization of protein and the solidification of protein and other deposits on the lenses.

Sterile saline can be used to clean and soak lenses. Such solutions are not always sterile though as certain microbes can live in a saline environment and spores are not totally inactivated by sterile saline solutions.

In the chemical means category, the use of so-called drugs, heavy metal-based antimicrobials such as thimerisol and trialkylammonium halides and compounds such as benzylalkonium chloride or similar compounds, have the potential problem of wearer discomfort if used incorrectly. The characteristics of such drugs which make them good microbiosides, also carry the possible phenomena of eye irritability. This phenomena is particularly present with the hydrogel type lens materials since the drug accumulates in the lens and is then released onto the eye during wear. Such drugs may cause eye discomfort for some people, sufficient to cause them to seek alternative means for sterilizing lenses.

In response to the problems with maintaining sterility with drugs, heat and saline, the use of oxidants has become an area of substantial interest for disinfecting contact lenses. Several two and one step systems based on peroxides have been developed for disinfecting contact lenses. One system is illustrated by U.S. Pat. No. 3,912,451 issued to C. Gaglia. Another is U.S. Pat. No. 4,473,550 issued to Rosenbaum, et al.

It has now been found that contact lenses may be simultaneously cleaned and disinfected by combining in one solution a peroxide for disinfecting and a peroxide-active enzyme for cleaning, particularly a peroxide-active proteolytic enzyme. Surprisingly, there is an increase in the effect of each individual component when presented in combination. That is, proteinaceous material removed is potentiated several fold by the presence of peroxide and the disinfecting rate is potentiated when the peroxide-active enzyme is present. The total result is that in one step, contact lenses can now be cleaned and sterilized more effectively than by independent use of the two components.

Peroxides and proteases have been combined in laundry detergents and for cleaning dentures. For example, U.S. Pat. No. 3,732,170 relates to a biological cleaning composition containing an enzyme and a source of peroxide, particularly an alkali-metal monopersulfate triple salt. The essence of this invention is a process for cleaning "proteinic" blood stains from a material, a laundry aid. This combination is noted to be formulated preferentially with an anionic detergent.

As another example, U.S. Pat. No. 4,155,868 recites a water soluble, effervescent denture cleanser tablet containing an enzyme and an active oxygen compound. The essence of this invention is the formulation of a tablet in such a manner as to prevent the premature inactivation of the enzyme by the oxidizing agent during storage.

Sodium perborate and enzymes are known components of modern laundry detergents. A review of this art is given by Oldenroth, O., in the German publication Fette Seifen Anstrichmittel, 1970 (72(7)), 582–7. This article indicates that the removal of denatured egg yolk from fabric is effected by bacterial proteases, but in the presence of perborates, the effectiveness of the proteases was decreased.

None of these disclosures teaches or contemplates the use of such compositions for cleaning and disinfecting contact lenses or the enhancement effect one component has on the activity of the other.

SUMMARY OF THE INVENTION

In one aspect, this invention relates to a method for the simultaneous cleaning and disinfecting of contact lenses, particularly one having a hydrophilic surface, which method comprises contacting the lenses with a solution comprises of a disinfecting amount of peroxide and an effective amount of peroxide-active proteolytic enzyme for a time sufficient to remove substantially all protein accretions and to disinfect the lenses.

SPECIFIC EMBODIMENTS

The concept of combining an enzyme and peroxide, to effect disinfecting and cleaning in one step can be applied to proteolytic, lipolytic and mucolytic enzymes, individually or in combination.

A peroxide-active enzyme is any enzyme having measurable activity at 3% (w/v) hydrogen peroxide in aqueous solution at standard temperature and pressure as determined by such colorimetric assays as the Azocoll method, Tomarelli, R. M., et al., J. Lab. Clin. Med., 34, 428 (1949), or the dimethyl casein method for determining proteolytic activity as described by Yaun Lin, et al., J. Biol. Chem., 244: (4) 789–793. (1969).

Enzymes may be derived from any plant or animal source, including microbial and mammalian sources. They may be neutral acidic or alkaline enzymes.

A proteolytic enzyme will have in part or in total the capacity to hydrolyze peptide amide bonds. Such enzymes may also have some inherent lipolytic and/or amylolytic activity associated with the proteolytic activity.

Preferred proteolytic enzymes are those which are substantially free of sulfhydryl groups or disulfide bonds, whose presence may react with the active oxygen to the detriment of both the activity of the active oxygen and which may result in the untimely inactivation of the enzyme. Metallo-proteases, those enzymes which contain a divalent metal ion such as calcium, magnesium or zinc bound to the protein, may also be used.

A more preferred group of proteolytic enzymes are the serine proteases, particularly those derived from Bacillus and Streptomyces bacteria and Asperigillus molds. Within this grouping, the more preferred enzymes are the Bacillus derived alkaline proteases generically called subtilisin enzymes. Reference is made to Deayl, L., Moser, P. W. and Wildi, B. S., "Proteases of the Genus Bacillus. II alkaline Proteases." Biotechnology and Bioengineering, Vol. XII, pp. 213–249 (1970) and Keay, L. and Moser, P. W., "Differentiation of Alkaline Proteases form Bacillus Species" Biochemical and Biophysical Research Comm., Vol. 34, No. 5, pp. 600–604, (1969).

The subtilisin enzymes are broken down into two sub-classes, subtilisin A and subtilisin B. In the subtilisin A grouping are enzymes derived from such species are B. subtilis, B. licheniformis and B. pumilis. Organisms in this sub-class produce little or no neutral protease or amylase. The subtilisin B sub-class is made up of enzymes from such organisms as B. subtilis, B. subtilis var. amylosaccharliticus B. amyloliquefaciens and B. subtilis NRRL B3411. These organisms produce neutral proteases and amylases on a level about comparable to their alkaline protease production.

In addition other preferred enzymes are, for example, pancreatin, trypsin, collaginase, keratinase, carboxylase, aminopeptidase, elastase, and aspergillo-peptidase. A and B, pronase E (from S. griseus) and dispase (from Bacillus polymyxa).

The identification, separation and purification of enzymes is an old art. Many identification and isolation techniques exist in the general scientific literature for the isolation of enzymes, including those enzymes having proteolytic and mixed proteolytic/amylolytic or proteolytic/lipolytic activity. The peroxide stable enzymes contemplated by this invention can be readily obtained by known techniques from plant, animal or microbial sources.

With the advent or recombinant DNA techniques, it is anticipated that new sources and types of peroxide stable proteolytic enzymes will become available. Such enzymes should be considered to fall within the scope of this invention so long as they meet the criteria for stability and activity set forth herein. See Japanese laid open application No. J6 0030-685 for one example of the production of proteases by recombinant DNA from Bacillus subtilis.

An effective amount of enzyme is to be used in the practice of this invention. Such amount will be that amount which effects removal in a reasonable time (for example overnight) of substantially all proteinaceous deposits from a lens due to normal wear. This standard is stated with reference to contact lens wearers with a history of normal pattern of protein accretion, not the very small group who may at one time or another have a significantly increased rate of protein deposit such that cleaning is recommended every two or three days.

The amount of enzyme required to make an effective cleaner will depend on several factors, including the inherent activity of the enzyme, the full extent of its synergistic interaction with the peroxide among several factors stand out as pertinent considerations.

As a basic yardstick, the working solution should contain sufficient enzyme to provide between about 0.001 to 5 Anson units of activity, preferably between about 0.01 and 1 Anson units, per single lens treatment. Higher or lower amounts may be used. Enzyme concentrations lower than these stated here probably will serve to clean the lens if sufficient time is allowed but such time may be so long as to be practically not useful in a usual lens cleaning and disinfecting regimen. Solution with higher activity should effect more rapid cleaning but may involve amounts of material which are too sizeable for practical cleaning purposes.

In weight/volume terms, since enzyme preparations are seldom pure, it is expected that the enzyme source will be used in amounts between about 0.003 to 15% of the final working solution. The precise amount will vary with the purity of the enzyme and will need to be finally determined on a lot-by-lot basis.

Enzyme activity is pH dependent so for any given enzyme, there will be a particular pH range in which that enzyme will function best. The determination of such range can readily be done by known techniques. It is preferred to manipulate the working solution to an optimum pH range for a given enzyme but such is not an absolute requirement.

The peroxide source may be any one or more compounds which gives active oxygen in solution. Examples of such compounds include hydrogen peroxide and its alkali metal salts, alkali metal perborate monohydrate and tetrahydrate, alkali metal persulfates, alkali metal carbonate peroxide, diperisophthalic acid, peroxydiphosphate salts and sodium aluminum aminohydroperoxide. Hydrogen peroxide and the sodium salts of perborates and persulfates are most preferred.

A disinfecting amount of peroxide means such amount as will reduce the microbial burden by one log in three hours. More preferably, the peroxide concentration will be such that the microbial load is reduced by one log order in one hour. More preferred are those peroxide concentrations which will reduce the microbial load by one log unit in 10 minutes or less.

A single peroxide concentration can not be made to apply to all peroxides as the percentage of active oxygen varies substantially between peroxides.

For hydrogen peroxide, on the lower side, a 0.5% weight/volume concentration will meet the first criteria of the preceding paragraph under most circumstances. It is preferred to use 1.0% to 2.0% peroxide, which concentrations reduce the disinfecting and cleaning time over that of the 0.5% peroxide solution. It is most preferred to use a 3% hydrogen peroxide solution through an amount of 10% may be used. No upper limit placed on the amount of hydrogen peroxide which can be used in this invention except as limited by the requirement that the enzyme retains proteolytic activity.

So far as other peroxides are concerned, the only limitation placed on their concentration is that they exhibit synergistic activity in combination with the peroxide-stable enzyme at a given concentration with regard to cleaning and disinfecting. For example, it has been found that sodium perborate at concentrations of 0.02% weight/volume will potentiate the enzymatic removal of protein from contact lenses. The appropriate concentrations of any given peroxide will be a matter finally to be determined through routine laboratory testing.

Additional materials may be added to the formulations, for example, tonicity agents, effervescing agents, stabilizers, binders, buffering agents, enzyme co-factors, disulfide bond reducing agents such as water-soluble mercaptans and salts of sulfites, pyrosulfites and dithionites and the like, agents to inactivate residual peroxide and the like.

Formulation of peroxide and enzyme may require stabilizing agents to prevent premature inactivation of both components. For solutions, it may be necessary or appropriate to add materials to stabilize the peroxide, particularly against metal-induced catalytic degradation. It may also be appropriate to add buffering agents to these solutions to maintain pH within a particular given range. Salts or other materials such as polyalcohols or the like may be added to modify the tonic value of such solutions.

In tablets or powders, the same considerations may be in effect in the sense of adding in salts, buffers and stabilizers so that when the tablet is dissolved, the appropriate pH and tonic value will be present. With tablets and powders it may also be appropriate to add effervescing agents. In addition, binders, lubricants for tableting purposes and any other excipients normally used for producing powders, tablets and the like, may be incorporated into such formulations. Indicators, colorants which indicate the presence or absence of peroxides may also be incorporated into these formulations.

To practice the invention, a solution of peroxide and enzyme is prepared and the lenses contacted with this solution, preferably by being immersed in the solution. The lenses will be left in contact with such solution long enough so that substantially all protein is removed from the lenses surfaces and the lenses are disinfected.

The method of sequence of combining the essential components to make up the solution which contacts the lenses will vary with the physical characteristics of the component employed; but order of addition is not critical to the practice of this invention. For example, if hydrogen peroxide is used it will not be reasonably possible to formulate a tablet or powder of all the components. Thus when hydrogen peroxide is not the peroxide source, it will be necessary to mix enzyme and other dry ingredients with aqueous peroxide. It is most convenient to formulate the enzyme and other dry components as a powder or tablet and to dissolve such material in a peroxide solution, then introduce the lenses into this solution. The lenses could already be in the peroxide solution when the enzyme is introduced but practical considerations make the first method the preferred one.

There is no particularly preferred form for the manufacturing of these materials. The two essential components may be formulated as separate components in dry or aqueous form. They may be combined in a single tablet or powder or one may be in dry form while the other is manufactured as an aqueous solution.

The final form will depend in part upon the type of peroxide source used in the formulation. It is anticipated that the powder or tablet form of this invention could also be in an effervescent form to enchance tablet breakup and to enhance the solubility rate of the ingredients. If a granular peroxide is employed, it will be possible to prepare powders and/or tablets from the several components of this invention. Where the peroxide is in solution form, it may be necessary to provide the enzyme from a second source in order to prevent long-term degradation of the enzyme.

Other energy input may be employed to potentiate the solution's cleaning and disinfecting effect. For example, ultrasonic devices are known to potentiate the speed at which proteases work in such circumstances as the cleaning and disinfecting rates.

The practice of this invention is not to be limited temperature-wise except by those temperature extremes which would substantially inactivate the proteolytic capability of the enzymes employed. Enzymatic activity is a function of temperature, some enzymes being considerably more labile than others to temperature extremes, particularly temperature increases. Other enzymes are heat stable and remain significantly active at temperatures of 70° C. or higher. Other enzymes retain substantial amounts of activity at or just above the freezing temperature of water. While the preferred temperature range for practicing this invention is between 20° and 37° C., particularly about 22°-25° C., it may be possible to practice this invention with certain peroxide-active enzymes in the temperature range between about 5° C. to 100° C.

One embodiment of this invention is to prepare a room temperature solution of enzyme and peroxide and to place this solution, along with the contact lens, in a contact lens heat disinfecting unit and run the unit through its the normal heat cycle. This is but one example of the heat variable aspects of this invention.

It is also contemplated that certain components may be separately prepared in a manner to effect the timed release of that component or to prevent interaction of component 1 with component 2 during tablet and powder preparation and subsequent storage. For example, in certain instances it may be appropriate to separately prepare the peroxide and the enzyme in a manner to prevent or reduce their interaction in a tableting process and upon subsequent storage thereafter.

In addition, solutions or powders may contain agents for detoxifying residual peroxide as part of the overall process of cleaning, disinfecting and ultimately the removal of residual peroxide. Enzymes which catalyze the conversion of peroxides to oxygen and water can be included in these formulations to remove residual peroxide in anticipation of inserting the lens back into the eye. For example catalases, organic enzymes which catalyze the degradation of peroxides, can be incorporated into tablets and powders, particularly in time-release form. Additionally, metals such as the heavy metal transition elements which catalyze the conversion of peroxide to oxygen and water, can be included in a powder or tablet formulation, again preferably in some delayed release form to provide a method for reducing to a non-toxic level any residual peroxide remaining in the solution after a given time interval. The use of transition metal catalysts for decomposing peroxides in a contact lens disinfecting solution is disclosed in U.S. Pat. No. 3,912,451, which information and technology is incorporated herein by reference as if set forth in full herein.

The following examples are set out to illustrate, but not limit, the scope of this invention.

EXAMPLE 1

Comparative Cleaning Effects

Twenty Hydrocurve® II 55% water lenses (Barnes-Hind, Inc. Sunnyvale, Calif., U.S.A.) were coated with heat-denatured lysozyme by placing the lenses in a phosphate buffered saline solution to which was then added sufficient lysozyme to make a 0.1% solution by weight. The lysozyme was from egg white. Individual vials were set up to contain 5 ml of the lysozyme solution and one fully hydrated lens. Vials were then heated for about 30 minutes at about 95° C. The lens was then removed, and after being cooled, was rinsed with distilled water and viewed to determine the type of lysozyme accretion.

Deposit classification: First the lens was wetted with normal saline, rubbed between thumb and finger, then grasped by the edge with plastic tweezers and rinsed with saline again. The anterior surface (convex surface) of the lens was viewed under the microscope at 100X. A film or deposit detected under these conditions was classified according to the percentage of surface which was covered by the film.

After the treatment described in the first paragraph, all lenses were found to have 100% of their anterior surface covered by thin-film protein deposits.

These lenses were then treated with solutions based on peroxide and the following enzyme formulations:

| Ingredient | Percentage (w/w) |
|---|---|
| Papain Tablet | |
| Sodium Borate, Dihydrate | 13.03% |
| Sodium Carbonate | 21.25% |
| Polyethylene glycol 3350 | 2.74% |
| Papain | 6.28% |
| Tartaric Acid | 13.71% |
| L-Cysteine HCL | 6.86% |
| EDTA | 5.04% |
| Sodium Chloride | 30.64% |
| Subtilisin A Tablet | |
| Sorbitol | 29.99% |
| N—acetylcysteine | 22.49% |
| Sodium Carbonate | 38.98% |
| Polyethylene glycol 3350 | 3.00% |
| Subtilisin A | 0.30% |
| Tartaric Acid | 5.24% |

The subtilisin A was obtained from Nova Industries of Denmark.

The lenses were divided into four groups of five. One group was treated 3% hydrogen peroxide. A second group was treated with the Subtilisin A containing formulation (133.4 mg. 0.4 mg subtilisin A) in 10 ml of a commercial saline product (Lensrins® made and sold by Allergan Pharmaceuticals, Inc.). A third group was treated with the Subtilisin A tablet dissolved in 10 ml of 3% hydrogen peroxide and the fourth group was treated with a 3% hydrogen peroxide (10 ml) containing one papain enzyme tablet (146.8 mg).

The lenses were allowed to soak for 3.5 hours. Then each group of lenses was treated appropriately to remove test solution and examined under a microscope to determine the extent of protein removal. The percent surface cleaned equaled the percent of the surface not covered by a protein film at 100X. The results are presented below.

Results were as follows:

| 3% Hydrogen Peroxide* | |
|---|---|
| LENS | % SURFACE CLEANED |
| A1 | 0 |
| A2 | 1 |
| A3 | 0 |
| A4 | 0 |
| A5 | 1 |

| SUBTILISIN A/Saline | | SUBTILISIN A/3% $H_2O_2$* | |
|---|---|---|---|
| LENS | % SURFACE CLEANED | LENS | % SURFACE CLEANED |
| B1 | 30 | C1 | 50 |
| B2 | 20 | C2 | 60 |
| B3 | 25 | C3 | 70 |
| B4 | 15 | C4 | 60 |
| B5 | 30 | C5 | 50 |

| PAPAIN/3% $H_2O_2$* | |
|---|---|
| LENS | % SURFACE CLEANED |
| E1 | 0 |
| E2 | 0 |
| E3 | 0 |
| E4 | 0 |
| E5 | 0 |

*Oxysept ® - 3% Hydrogen peroxide solution marketed by Allergan Pharmaceuticals Inc.

While the hydrogen peroxide and papain/hydrogen peroxide cleaning activity was essentially nil, subtilisin and 3% hydrogen peroxide cleaned between 50 and 70% of the contact lens surface area. Secondly, subtilisin A alone without peroxide cleaned between 15 and 30% of the lens surface while in comparison, subtilisin A with 3% peroxide cleaned between 50 and 70% of the lens surface. Subtilisin A and peroxide was approximately twice as effective in its cleaning capacity in comparison with subtilisin without peroxide.

EXAMPLE 2

Peroxide/Enzyme Activity

Fifteen Hydrocurve II® lenses (Barnes-Hind) were exposed to lysozyme and the presence of Type IV protein accretion confirmed as described in Example 1.

Five lenses each were soaked for eight hours in the following solutions: 3% hydrogen peroxide (Oxysept 1 produced by Allergan Pharmaceuticals, Inc.); a commercially available, pancreatin containing enzyme tablet (Opti-Zyme® tablet manufactured by Alcon) dissolved in 10 ml of saline solution (Boil-'n-Soak®, a normal saline solution produced by Alcon); and a solution of pancreatin enzyme (Opti-Zyme®) in 10 ml of 3% hydrogen peroxide (Oxysept® 1).

Following an 8 hour soak, lenses were treated to remove residual soaking solution and the percentage of protein determined as described in Example 1. The results were as follows:

| 3% Hydrogen Peroxide | |
|---|---|
| Lens | % Surface Cleaned |
| A1 | 0 |
| A2 | 0 |
| A3 | 0 |
| A4 | 0 |
| A5 | 0 |

| Pancreatin/Peroxide Solution | | Pancreatin/Normal Saline | |
|---|---|---|---|
| Lens | % Surface Cleaned | Lens | % Surface Cleaned |
| B1 | 90 | C1 | 0 |
| B2 | 85 | C2 | 0 |
| B3 | 85 | C3 | 0 |
| B4 | 90 | C4 | 0 |
| B5 | 80 | C5 | 0 |

The combination of the pancreatin-containing enzyme tablet and 3% peroxide effected substantial cleaning while the peroxide alone and the enzyme alone had no detectable protein removing effect in the 8 hours of soaking time used here.

EXAMPLE 3

Effect of Peroxide Concentration

Hydrocurve® lenses were coated with lysozyme as per Example 1. The subtilisin tablet formulation used here was the same as in Example 1 except that the N-acetylcysteine was removed. Five different levels of hydrogen peroxide were used, beginning at a concentration of 0.5% by weight/volume. The control was the tablet without peroxide with the tonicity value adjusted to approximately that of the 0.5% peroxide/enzyme solution with sodium chloride. The pH was adjusted to between about 9.0–9.03 in each solution with hydrochloric acid. Five lenses were treated for three hours at room temperature with 10 ml of each solution. The amount of protein (percentage) removed from the lens surface is given in Table I.

TABLE I

Effects of Peroxide Concentration on Cleaning Efficacy

| | Enzyme Conc. | pH | Tonicity | % peroxide Weight/vol. | % Lens Cleaning |
|---|---|---|---|---|---|
| A | 0.04 mg/ml | 9.025 | 318 mOsm/kg | 0 | 9.0 (5.5) |
| B | 0.04 mg/ml | 9.086 | 330 mOsm/kg | 0.5% | 44.0 (8.9) |
| C | 0.04 mg/ml | 9.016 | 390 mOsm/kg | 1.0% | 78.0 (2.7) |
| D | 0.04 mg/ml | 9.022 | 643 mOsm/kg | 1.5% | 87.0 (2.7) |
| E | 0.04 mg/ml | 9.023 | 796 mOsm/kg | 2.0% | 94.0 (4.2) |
| F | 0.04 mg/ml | 9.016 | 932 mOsm/kg | 2.5% | 97.0 (2.7) |

EXAMPLE 4

Evaluation of Antimicrobial Activity of Subtilisin in 3% Hydrogen Peroxide

The effect of a tableted formulation containing subtilisin A (given in Example I) on the antimicrobial activity of hydrogen peroxide when dissolved in 3% hydrogen peroxide (Lensan A. Allergan Pharmaceuticals, Inc.) was tested against the panel of micro-organisms required by the U.S. FDA guidelines for testing contact lens solutions for disinfective efficacy. Standard culture methods, harvest and quantitative microbiological analysis techniques were used. The organisms used were S. marcescens. ATCC 14756 or 14041: S. aureus, ATCC 6538: P. aeruginosa, ATCC 9027 or 15442: E. coli, ATCC 8739, C. albicans, ATCC 10231 and A. niger. ATCC 16404. A 133.4 mg tablet of the subtilisin A formulation (0.04 mg) given in Example 1 was used.

The results of this study are given in Table 1.

TABLE I

COMPARISON OF EXTRAPOLATED D-VALUES* IN MINUTES

| | Study I | | Study II | |
|---|---|---|---|---|
| ORGANISMS | 3% $H_2O_2$ | 3% $H_2O_2$ + SUB. A | 3% $H_2O_2$ | 3% $H_2O_2$ + SUB. A |
| S. marcescens | 2.5 | 1.7 | 3.5 | 1.3 |
| S. aureus | 4.0 | 3.0 | 4.0 | 2.0 |
| P. aeruginosa | 0.3 | 0.5 | 0.3 | 0.1 |
| E. coli | 2.5 | 0.9 | 1.7 | 0.2 |
| C. albicans | 36.5 | 13.0 | 15.0 | 9.0 |
| A. niger | 9.5 | 11.6 | 6.0 | 6.0 |

*D-value is the time required to reduce a microbial challenge of $5 \cdot 10^6$ organisms per ml by 90% or 1 logarithm The control, an enzyme tablet in saline, showed no antimicrobial activity over a 24 hour period.

A second study similar in design and following the same procedure as the first was performed. The results are also presented in Table I.

Table II lists the average kill rates for the data presented in Table I.

TABLE II

AVERAGE KILL RATES (D-VALUES) IN MINUTES AT ROOM TEMPERATURE

| ORGANISMS | 3% $H_2O_2$ | 3% $H_2O_2$/SUB. A |
|---|---|---|
| S. marcescens | 3.0 | 1.5 |
| E. coli | 2.1 | 0.6 |
| P. aeruginosa | 0.3 | 0.3 |
| S. aureus | 4.0 | 2.5 |
| C. albicans | 26.0 | 11.0 |
| A. niger | 8.0 | 9.0 |

Since the lower the D value, the more effective the antimicrobial activity, each of these studies demonstrates that 3% hydrogen peroxide and subtilisin A together are a substantially more effective disinfecting composition than either of the two components acting separately.

EXAMPLE 5

Testing of Preservative Efficacy

Three panels of organisms, one based on the USP XXI panel, another soft contact lens panel containing representative organisms required by the FDA for antimicrobial efficacy testing of contact lens disinfection products and a third "isolates" panel comprised of selected organisms which commonly are encountered as natural flora of either the human body or the environment and which may be deposited on contact lenses or become innoculated into contact lens solutions, were used in testing the differential between the extrapolated D-values of 3% hydrogen peroxide (Oxysept I, Allergan Pharmaceuticals, Inc.) with and without subtilisin A. The organisms tested are listed in the tables appended hereto.

The micro-organisms were prepared by standard microbiological techniques. Each sample was tested in duplicate. As a first step in the assay, 10 ml of 3% hydrogen peroxide was pipetted into screw-cap test tubes. Into selected tubes was added one tablet of subtilisin A, whose composition is described in Example 1. The subtilisin-containing tubes were vortexed for approximately 2 minutes to dissolve the subtilisin tablet. Immediately the challenge organism was added to the tube. After a predetermined contact time interval, survivors were quantified in CFU/ml.

A D-value was calculated by extrapolation from kill curves using an aerobic plate count method. This method worked essentially as follows: An aliquot of test solution was removed immediately after the predetermined contact interval, divided in half and dispersed into two test tubes containing neutralizer media. A serial ten-fold dilution of the neutralizer media was prepared in a manner to compensate for the expected level of recovery. For low level recovery, a small aliquot was transferred directly onto a neutralizer agar plate. For the other three serial dilution tubes, an equal volume of sample was placed on neutralizer agar plates. All plates were incubated at 35°-37° C. for 2-7 days, or longer if required. Colony counts were then recorded and D-values calculated as follows: All plate counts for each time interval were averaged. The averaged data was plotted on a semi-log graph paper with the numbers of survivors on the ordinate and the contact time on the abscissa. The starting point (inoculum level) was connected to the first point yielding less than 10 organisms per ml by a straight line. The slope of this line extrapolated to zero gives the D-value. This is otherwise referred to as "end-point analysis".

TABLE III

Extrapolated Kill Rates (D-valves) of 3% Hydrogen Peroxide (Oxysept I) With and Without Subtilisin

| Organism and ID # | Without Subtilisin | With Subtilisin |
|---|---|---|
| (1) USP XXI Panel | | |
| Serratia marcescens. ATCC #14756 | 1.4 min. | 1.0 min. |
| Staphylococcus aureus. ATCC #6538 | 3.4 min. | 2.1 min. |
| | 3.2 min. | 2.6 min. |
| Pseudomonas aeruginosa. ATCC #9027 | 0.2 min. | 0.2 min. |
| Escherichia coli. ATCC #8739 | 1.0 min. | 0.3 min. |
| Candida albicans. ATCC #10231 | 20.0 min. | 13.0 min. |
| Aspergillus niger. ATCC #16404 | 10.0 min. | 8.0 min. |
| (2) "Soft Lens", Panel (FDA) | | |
| Serratia marcescens. ATCC #14041 | 1.7 min. | 1.5 min. |
| Staphylococcus epidermidis. | 0.8 min. | 1.5 min. |
| ATCC #17917 | 0.4 min. | 1.0 min. |
| Pseudomonas aeruginosa. ATCC #15442 | 0.6 min. | 0.3 min. |
| Aspergillus fumigatus. ATCC #10894 | 13.5 min. | 2.5 min. |
| Candida albicans. ATCC #10231 | 20.0 min. | 13.0 min. |
| (3) Various Isolates | | |
| Klebsiella pneumoniae. ATCC #13883 | 1.1 min. | 0.6 min. |
| Pseudomonas cepacia. ATCC #17765 | 0.4 min. | 0.2 min. |
| Proteus mirabilis. CSULB/VA | 1.2 min. | 1.0 min. |
| | 1.3 min. | 0.9 min. |
| Proteus vulgaris. ATCC #17313 | 0.4 min. | 0.3 min. |
| Candida parapsilosis. PM 4064 | 63.0 min. | 55.0 min. |
| Penicillium sp. (Aqua Tar isolate II) | 2.5 min. | 2.1 min. |

EXAMPLE 6

Comparative Enhancement of Peroxide With and Without Enzyme

Comparative enhancement of the antimicrobial kill rates of various solutions of 3% hydrogen peroxide due to the addition of the enzyme subtilisin. The figures in Table IV represent the percentage of decrease in the D-value for a particular peroxide solution plus the subtilisin tablet of Example 1 over that of the particular peroxide solution alone. The AO-Sept system employed a heavy metal catalyst (platinum coated disc) in the vials to degrade peroxide as per U.S. Pat. No. 3,912,451.

TABLE IV

| Organism | Lensan A (Data From Table II) | Oxysept I (Data From Table III) | AO Sept |
|---|---|---|---|
| Serratia marcescens | 50% | 29% | 88% |
| Escherichia coli | 71% | 70% | 90% |
| Pseudomonas aeruginosa | 0 | 0 | 20% |
| Staphylococcus aureus | 38% | 28% | 60% |
| Candida albicans | 58% | 35% | 33% |
| Aspergillus niger | 0% | 20% | 32% |

These figures demonstrate that each of the 3% peroxide solutions is a much more effective disinfectant when subtilisin A is present. The effect is particularly pronounced in the AO-Sept system.

EXAMPLE 7

Effect of Peroxide Concentration on Enzyme Activity

The enzymatic activity of the subtilisin A tablet described in Example 1 and trypsin was determined at different hydrogen peroxide concentrations using the Modified Azocoll method "Sigma Catalog". Baker Chemical Company, 30% hydrogen peroxide was used. Appropriate dilutions were made with a 0.2M borate buffer at about pH 8.4. Azocoll substrate and trypsin were obtained from Sigma Corporation.

Peroxide was first diluted with buffer to the appropriate concentrations. One enzyme tablet was dissolved in 10 ml of buffer to which had been added 50 mg of Azocoll substrate. One ml of this solution was then added to each of the peroxide concentrations, the enzyme/substrate buffer solution being the control. After mixing, the reaction was run at room temperature for 2 minutes, then quenched with 2 ml of 10% trichloroacetic acid, which precipitated the enzyme. Residual color measurements were measured at 520 nm. Subtilisin results are given in Table IV, trypsin results in Table V.

TABLE IV

Subtilisin Activity in Hydrogen Peroxide

| % $H_2O_2$ | OD 520 |
|---|---|
| 0 | 0.27 |
| 1 | 0.39 |
| 2 | 0.57 |
| 3 | 0.56 |
| 4 | 0.66 |
| 4.5 | 0.56 |
| 5 | 0.68 |
| 6 | 0.68 |
| 8 | 0.90 |
| 30 | 0.91 |

TABLE V

*Trypsin Activity in Hydrogen Peroxide

| % $H_2O_2$ | OD 520 |
|---|---|
| 03 | .5 |
| 30 | .6 |

*10 mg of trypsin powder were added to the $H_2O_2$ solution.

Table IV indicates that subtilisin A is active in Azocoll assay throughout a broad range of peroxide concentrations. The activity at 30% peroxide is approximately the same as at the 8% concentration. Enzyme activity for subtilisin A apears to be saturated at hydrogen peroxide concentrations between 2-6%. Table V indicates that trypsin is active in hydrogen peroxide.

EXAMPLE 7

Effects of Perborate on Enzyme Activity

Hydrocurve II® lenses were coated with heat-denatured lysozyme as per the procedure described in Example 1. The following solutions based on subtilisin A (Novo Industries, Denmark) and sodium perborate were prepared to test the combined effects of perborate as a source of peroxide on the proteolytic activity of subtilisin A. Solution A—0.04 mg/ml subtilisin A, bicarbonate buffer to adjust the pH to 8.307; Solution B—0.02% (w/v) sodium perborate, bicarbonate buffer, pH adjusted to 8.533; and Solution C—0.04 mg/ml subtilisin A, 0.02% (w/v) sodium perborate, bicarbonate buffer, pH adjusted to 8.532. Each treatment was done in a 10 ml volume.

Five protein coated lenses were soaked in each of these solutions (10 ml) for 3 hours at room temperature. All lenses were then rinsed and the amount of residual protein determined. Table VI gives the average percentage of surface cleaned after these treatments.

TABLE VI

Comparative Cleaning of Enzyme With and Without Peroxide

| Solution | Average % Surface Cleaned |
|---|---|
| A | 9.0 ± 5.6 |
| B | 0 |
| C | 30.0 ± 12.2 |

What is claimed is:

1. A method for the simultaneous cleaning and disinfecting of contact lenses which method comprises contacting the lenses with a solution comprised of a disinfecting amount of peroxide and an effective amount of peroxide-active proteolytic enzyme for a time sufficient to remove substantially all protein accretions and to disinfect the lenses.

2. The method of claim 1 wherein the solution is prepared by combining the enzyme and peroxide at the time the lenses are contacted with the solution.

3. The method of claim 2 wherein the enzyme is in a powder or tablet form and is dissolved in the peroxide solution.

4. The method of claim 1 wherein the solution is prepared by dissolving a dry peroxide and dry enzyme in an aqueous solution.

5. The method of claim 4 wherein both components are combined in powder or tablet form.

6. The method of claim 2 wherein the enzyme is present in an amount between 0.001 and 5 Anson units and the peroxide is hydrogen peroxide and is present in an amount between 0.02 and 10% by weight/volume.

7. A method according to claim 6 where the proteolytic enzyme is subtilisin.

8. The method of claim 7 wherein the peroxide is hydrogen peroxide, sodium perborate, potassium persulfate, sodium percarbonate, diperisophthalic acid, peroxydiphosphate salts or sodium aluminum aminohydroperoxide.

9. The method of claim 8 where the [aqueous composition] *solution* comprises 3% hydrogen peroxide and 0.30% subtilisin A by weight/volume.

*10. The method of claim 1 wherein said contact lenses have a hydrophilic surface.*

*11. The method of claim 10 wherein said peroxide-active proteolytic enzyme is a subtilisin enzyme.*

*12. The method of claim 11 wherein said subtilisin enzyme is subtilisin A.*

*13. The method of claim 10 wherein said peroxide is hydrogen peroxide in an amount between 0.02 and 10% by weight/volume.*

*14. The method of claim 13 wherein said hydrogen peroxide is present in an amount of about 3% by weight-/volume.*

*15. The method of claim 10 wherein said peroxide-active proteolytic enzyme is subtilisin A and said peroxide is hydrogen peroxide.*

• • • • •